United States Patent [19]

Bishop et al.

[11] Patent Number: 5,595,905

[45] Date of Patent: Jan. 21, 1997

[54] PROCESS CONTROL SYSTEM FOR FED-BATCH FERMENTATION USING A COMPUTER TO PREDICT NUTRIENT CONSUMPTION

[75] Inventors: Bruce F. Bishop, Wentzville; Rodney G. Combs, Manchester; Saied Banankhah, Chesterfield, all of Mo.

[73] Assignee: G.D. Searle & Co., Skokie, Ill.

[21] Appl. No.: 289,610

[22] Filed: Aug. 12, 1994

Related U.S. Application Data

[63] Continuation of Ser. No. 849,847, Mar. 12, 1992, abandoned.

[51] Int. Cl.$^6$ .............................. C12N 1/00; C12N 5/00; G05B 21/02; G05B 23/02

[52] U.S. Cl. ........................ 435/243; 364/130; 364/178; 364/550; 364/579; 435/240.1; 435/286.1; 435/286.5; 435/287.1; 435/289.1

[58] Field of Search ................................. 435/240.1, 243, 435/291; 364/130, 178, 550, 579, 221, 223.3

[56] References Cited

U.S. PATENT DOCUMENTS

| | | | |
|---|---|---|---|
| 4,444,882 | 4/1984 | Shimizu | 435/3 |
| 4,891,310 | 1/1990 | Shimizu et al. | 435/3 |
| 4,893,935 | 1/1990 | Mandel et al. | 356/436 |
| 4,945,060 | 7/1990 | Turner et al. | 435/291 |
| 4,948,736 | 8/1990 | Kobayashi et al. | 435/311 |
| 4,992,942 | 2/1991 | Bauerle et al. | 364/420 |

OTHER PUBLICATIONS

"An Automatic, On–Line Glucose Analyzer for Feed–Batch Growth of *Escherichia coli*", *Biotechnology Techniques*, vol. 1, No. 4, pp. 225–230 (1987).

"Comparison of Growth, Acetate Production and Acetate Inhibition of *Escherichia coli* Strains in Batch and Fed-–Batch Fermentations", *Applied and Environmental Microbiology*, Apr. 1990, pp. 1004–1011.

"Effects of Fermentation Feeding Strategies Prior to Induction of Expression of a Recombinant Malaria Antigen in *Escherichia coli*", *Journal of Industrial Microbiology*, 2, pp. 87–95 (1987).

"Production of Recombinant Human Growth Hormone in *Escherichia coli*: Expression of Different Precursors and Physiological Effects of Glucose, Acetate, and Salts", *Biotechnology and Bioengineering*, vol. 36, pp. 1–11, (1990).

"Control of Carbon Flux to Acetate Excretion During Growth of *Escherichia coli* in Batch and Continuous Cultures", *Journal of General Microbiology*, (1989), 135, 2875–2883.

"Growth of *E. coli* W to High Cell Concentration by Oxygen Level Linked Control of Carbon Source Concentration", *Biotechnology and Bioengineering*, vol. XXIII, pp. 1015–1021, (1981).

"Glucose as a Substrate in Recombinant Strain Fermentation Technology", *Appl. Microbiol. Biotechnol.*, (1989), 31:163–167.

"Factors Influencing Productivity of Fermentations Employing Recombinant Microorganisms", *Enzyme Microb. Technol.*, (1986), vol. 8, Dec.

"Physiological Constraints in Increasing Biomass Concentration of *Escherichia coli* B in Fed–Batch Culture", *Biotechnology Letters* vol. 9, No. 2, pp. 89–94 (1987).

"Glucose–Limited Fed–Batch Cultivation of *Escherichia coli* with Computer–Controlled Fixed Growth Rate", *Biotechnology and Bioengineering*, vol. 35, pp. 312–319 (1990).

"Effect of Operating Parameters on Specific Production Rate of a Cloned–Gene Produce and Performance of Recombinant Fermentation Process", *Biotechnology and Bioengineering*, vol. 35, pp. 287–295 (1990).

"Maximizing the Expression of Recombinant Proteins in *Escherichia coli* by Manipulation of Culture Conditions", *Journal of Fermentation and Bioengineering*, vol. 69, No. 3, 159–165, (1990).

"Prokaryotic Secretion", *Cell*, vol. 61, 739–741, (1990).

"Communications to the Editor, In Situ Glucose In Fermentation Broth by Sandwiched Glucose–Oxidase Electrode (SGE)", *Biotechnology and Engineering*, vol. 35, pp. 103–107 (1990).

"Application of a Microcomputer–Based System to Control and Monitor Bacterial Growth", *Applied and Environmental Microbiology*, pp. 239–244), (1984).

"A Predictive and Feedback Control Algorithm Maintains a Constant Glucose Concentration in Fed–Batch Fermentations". Applied and *Environmental Microbiology*, Apr. 1991, pp. 910–917. vol. 57, No. 4.

Luli et al , *Biotech. Tech.* 1, No. 4, 225–230 (1987).

Luli et al, *App. Environ Micro.* 1004–1011 (Apr. 1990).

Jensen et al, *Biotech Bioengineer* 36 1–11 (1990).

El–Mansi et al, *Journal Gen. Micro.* (1989), 135, 2875–2883.

Gleiser et al, *Biotech and Bioengineer.*, 23, 1015–1021 (1981).

Rinas et al, *Appl. Microbiol. Biotechnol.*, 31, 163–167 (1989).

(List continued on next page.)

*Primary Examiner*—John W. Rollins
*Assistant Examiner*—Deborah K. Ware
*Attorney, Agent, or Firm*—Joseph W. Bulock; Dennis A. Bennett

[57] ABSTRACT

A method for controlling nutrient concentration levels in a fermentation broth containing bacteria or a yeast and a nutrient is disclosed. A computer calculates the nutrient consumption rate of the broth for selected intervals of time between successive samples in real time by comparing the nutrient concentrations of the samples. Thus, the computer having the capability to predict an estimated rate at which the nutrient concentration is expected to decrease at selected sample intervals. Further, adding fresh nutrient to the fermentation broth at a rate and quantity based on the estimated rate to control nutrient concentration levels. Furthermore, a means for obtaining a series of samples and measuring nutrient concentrations is also disclosed.

12 Claims, 7 Drawing Sheets

OTHER PUBLICATIONS

Zabriskie et al, *Enzyme Microb. Technol.*, 8 706–717 (1986).
*Biotech. Letters*, 9, No. 2, 89–94 (1987).
Paalme et al., *Biotech and Bioengineer* 35, 312–319 (1990).
Park et al, *Biotech and Bioengineer*, 35, 287–295 (1990).
Galindo et al, *Jour. Fermentation and Bioengineer*, 69, No. 3, 159–165 (1990).
Model et al, *Cell*, 61, 739–741 (Jun. 1, 1990).
Rishpon et al, *Biotech and Bioengineer*, 35, 103–107 (1990).
Titus et al, *Appl. & Environ. Microbiol.*, 47, No. 2, 239–244 (Feb. 1984).
Kleman et al, *Appl & Environ. Microbiol.*, 57, No. 4, 910–917 (Apr. 1991).

SAMPLING PERIOD

S1 = START SAMPLE CYCLE AT TIME 1
S2 = START 2ND SAMPLE CYCLE AT TIME 2
Y1 = START SAMPLE INTO YSI
Y2 = START SAMPLE 2 INTO YSI
R1 = RECEIVE YSI DATA OUTPUT
R2 = RECEIVE YSI DATA OUTPUT

F = FLUSH TIME
P1 = OLD PUMP RATE (FROM Y1 TO R1)
P2 = NEW PUMP RATE (FROM R1 TO Y2)

GLUCOSE CONTROL EQUATIONS

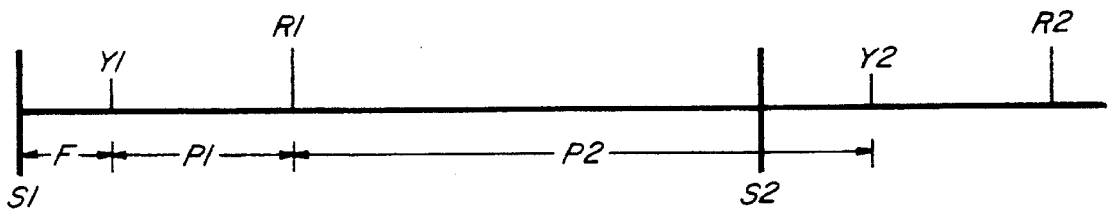

1. SAMPLING INTERVAL (MIN) = (S2-S1)/60

2. VOLUMETRIC PUMP FLOW = VOL ADDED FROM Y1 TO Y2 (ML)

$$\frac{[R1-(S1+F)](P1)}{60} + \frac{[(S2+F)-R1](P2)}{60}$$

3. TOTAL GLUCOSE ADDED FROM Y1 TO Y2 (g/l)

$$\frac{(VOL.\ PUMP\ FLOW)(GLUCOSE\ FEED\ CONCENTRATION)}{TOTAL\ VESSEL\ VOLUME}$$

4. GLUCOSE CONSUMPTION RATE FROM Y1 TO Y2 (g/l/MIN)

$$\frac{[GLU]\ AT\ Y1 - [GLU]\ AT\ Y2 + TOTAL\ GLUCOSE\ ADDED}{SAMPLING\ INTERVAL}$$

5. CALCULATE NEW PUMP RATE (ML/MIN)

$$\frac{(GLUCOSE\ CONSUMPTION\ RATE)(TOTAL\ VESSEL\ VOLUME)}{GLUCOSE\ FEED\ CONCENTRATION}$$

GLUCOSE SETPOINT CONTROL EQUATIONS

1. SETPOINT CORRECTION (ML/MIN)

$$\frac{(GLUCOSE\ SETPOINT - Y2)(TOTAL\ VESSEL\ VOLUME)}{(GLUCOSE\ FEED\ CONC.)(SAMPLING\ INTERVAL)/60}$$

2. ERROR COMPENSATION = 1.0 +/- (SETPOINT - Y2) (K)

3. CORRECTED FLOW = NEW PUMP RATE (ERROR COMP.)

Fig. 3b

PROCESS CONTROL SYSTEM FOR FED-BATCH FERMENTATION USING A COMPUTER TO PREDICT NUTRIENT CONSUMPTION

RELATED CASES

This is a continuation of U.S. application Ser. No. 07/849,847, filed Mar. 12, 1992, now abandoned.

BACKGROUND OF THE INVENTION

1. Field of the Invention

The present invention relates to fed-batch fermentation, and more particularly to computer automated feed-back control of the nutrient level of a broth in fed-batch fermentation.

2. Description of the Prior Art

During fermentation processes, the bacteria or yeasts growing in a fermentation broth consume nutrient at a variable rate related to, among other things, the microorganism density and rate of growth. In the case of fed-batch fermentation of bacteria, for example, the rate of consumption of nutrient, typically, glucose, can increase exponentially with time until affected by the limitations of the environment or alteration of the conditions, such as varying the rate of agitation and aeration. Another process interference results from the introduction of chemical agents for inducing the bacteria to produce recombinant DNA products. Accordingly, the yield or productivity of a fermentation process is increased when nutrient is added during the fermentation to compensate for that depleted through consumption by the bacteria.

It is desirable to maintain a constant nutrient concentration throughout the fermentation process despite the variable rate at which the nutrient is depleted. When nutrient concentration, usually glucose, is very high, undesirable waste by-products, usually acetic acid, lactic acid or ethanol are produced. The economic implications of inefficient nutrient utilization are very important because of the high cost of glucose. When the nutrient concentration is too low, or absent, the growth of the microorganisms is restricted usually resulting in reduced productivity of the process. Thus, significant efforts have been expended in attempting to develop methods for maintaining the nutrient concentration relatively constant during the fermentation process. Nevertheless, completely satisfactory techniques have not been found to maintain the concentration within a sufficiently desirable narrow range, especially in the situations in which the standard exponential consumption rate is disrupted.

Generally, manual techniques have been employed for controlling the nutrient concentration by measuring the nutrient level of the medium and replenishing the nutrient to compensate for depletion. Recent reports have described the development of at least partially automated techniques. For example, in G. Luli et al., "An Automatic, On-Line Glucose Analyzer for Feed-Back Control of Fed-Batch Growth of *Escherichia coli*", Biotechnology Techniques, Vol. 1, No. 4, pp. 225–230 (1987), a process control technique for maintenance of glucose concentration is described in which the glucose level is monitored periodically and matched against archived profiles of glucose consumption rate versus time as determined by earlier experimentation. The amount of glucose to be introduced during the next interval is then determined according to the archived curve. This process also required the separation of cells from the broth by membrane filtration prior to analysis of the cell-free medium for nutrient concentration. Glucose concentrations were maintained between 1.0 and 2.0 grams per liter with this method.

In a later paper, G. Lull et al., "Comparison of Growth, Acetate Production and Acetate Inhibition of *Escherichia coli* Strains in Batch and Fed-Batch Fermentations", Applied and Environmental Microbiology, April 1990, pp. 1004–1011, a similar technique with a higher sampling rate is discussed. The article reports that archived data for glucose consumption rates were required for computer-controlled glucose addition. The glucose concentration is reported to have been maintained at about 1.0+/−0.2 g/l.

G. Kleman et al., "A Predictive and Feedback Control Algorithm Maintains a Constant Glucose Concentration in Fed-Batch Fermentations", Applied and Environmental Microbiology, April 1991, pp. 910–917, describes a method which requires linear regression analysis of nutrient concentrations to feed-forward control the addition of nutrient to match consumption rate (glucose demand, GD). The method assumes that the theoretical glucose demand is based on a constant yield of biomass from glucose. The method requires cell-free broth for analysis of nutrient concentration requiring frequent broth sampling at two minute intervals and has a response time between sample analysis and nutrient pump response.

However, such techniques suffer from several drawbacks. The technique of Luli et al. requires that numerous trials of the particular strain of microorganism under various conditions and desired nutrients and nutrient concentrations be conducted to prepare an archive of nutrient consumption rate curves for comparison purposes. In addition, because the nutrient feed rate is dependent on the archived curve, a curve for the same strain being cultivated under the same conditions must be located in order to predict the rate of consumption of the nutrient during the next time interval. Further, if the fermentation conditions change, for example, if the agitation rate is varied or if a chemical agent is introduced to induce the microorganism to produce recombinant DNA products, archived curves cannot be relied on. The requirement for cell-free broth for nutrient analysis adds another level of complexity to the method. Although the second Luli et al., article makes reference to control of glucose concentration at 1.0 gram per liter +/−0.2 grams per liter, it appears that such control is maintained only for undisturbed fermentation conditions with standardized strains of *Escherichia coli*. Again the major limitations of this method is that this system does not adapt to variances from the conditions under which the archived consumption rate curves were derived, and cell-free broth is required for nutrient analysis. Kleman et al., requires a linear regression analysis in the algorithm and is therefore a major limitation to the method. When glucose consumption rates are very high the method significantly underpredicts glucose demand. Further, linear regression analysis for determining glucose demand during metabolic shifts creates errors in response to matching glucose demands and feed rates.

SUMMARY OF THE INVENTION

Briefly, therefore, the present invention is directed to a novel method for controlling nutrient concentration at a desired level in a broth undergoing fermentation by microorganisms in the broth. A method for controlling nutrient concentration levels in a broth under the control of a computer, comprising the steps of:

a. fermenting a broth containing microorganisms and a nutrient;

b. withdrawing a series of samples of the broth, the samples being withdrawn at periodic intervals;

c. measuring the nutrient concentrations of samples in the series;

d. comparing the nutrient concentration of a designated sample with the nutrient concentration of a preceding sample withdrawn before the designated sample;

e. determining the nutrient utilization rate in real-time by comparing the nutrient concentration of the designated sample with that of the preceding sample, the calculated rate at which the nutrient concentration of the broth decreased during a designated interval extending from the time which the preceding sample was withdrawn to the time at which the designated sample was withdrawn;

f. comparing the calculated rate at which the nutrient concentration of the broth decreased during the designated interval to the rate at which the nutrient concentration of the broth decreased during at least one interval preceding the designated interval;

g. predicting from comparing such rates an estimated rate at which the nutrient concentration of the broth is expected to decrease in an interval succeeding the designated interval; and h. adding fresh nutrient to the broth at a rate and quantity based on the estimated rate.

The present invention is also directed to a method for culturing microorganisms in a medium containing glucose, wherein the glucose concentration is regulated at a selected level in the range of from about 0.2 g/l to about 1 g/l.

It is an objective of the present invention to provide an improved method for controlling nutrient concentration at a desired level in a broth undergoing fermentation by microorganisms in a broth.

It is an advantage of the present invention to provide control of the nutrient concentration of a broth at a desired level without the need for comparative test runs and despite disturbances to the fermentation processes.

It is another advantage of the present invention to better predict nutrient demand of a broth undergoing fermentation, when consumption rates are elevated.

BRIEF DESCRIPTION OF THE DRAWINGS

FIG. 3a, 3b are terms and equations used in the invention.

DESCRIPTION OF THE PREFERRED EMBODIMENTS

In accordance with the present invention, it has been discovered that improved control of nutrient concentration in a fermentation broth may be achieved by periodically sampling a fermentation broth for nutrient concentration, calculating the nutrient consumption rate by comparing the nutrient concentration of the sample to a concentration determined from an earlier sample, and then comparing that consumption rate to those calculated from earlier samples to predict the consumption rate over the next time period and introducing fresh nutrient accordingly. It is intended that the present invention is capable of controlling the concentration of any nutrient which can be measured. It is envisioned that a computer is the optimal device for this method. This process, which may be conducted automatically, has been found to provide many advantages over conventional techniques. For example, it obviates the necessity for creating an archive of nutrient consumption rate profiles. In addition, it permits maintenance of nutrient level within a narrow range. Not only that, but good control of nutrient level has been found to be possible even for nonstandard fermentation broths (even involving recombinant strains), for fermentations under varying conditions and for fermentation processes that are disturbed by the introduction of agents for inducing protein production.

Moreover, because of the great precision afforded by this method, nutrient concentration has been regulated at lower levels than previously employed and it has been found that such lower levels surprisingly result in improved expression of recombinant protein. In other words, a method has been discovered by which yield of recombinant protein can be increased. And because the improved yield is achieved with a lower glucose concentration, it can be achieved at lower cost. Preferable *E. Coli* is fermented at a nutrient setpoint of 0.20 grams per liter for optimum glucose conversion and for optimum production of rDNA proteins. All prepared proteins in this method is bovine prolactin (BPRL) and bovine placental lactogen (BPL).

Figure 1:
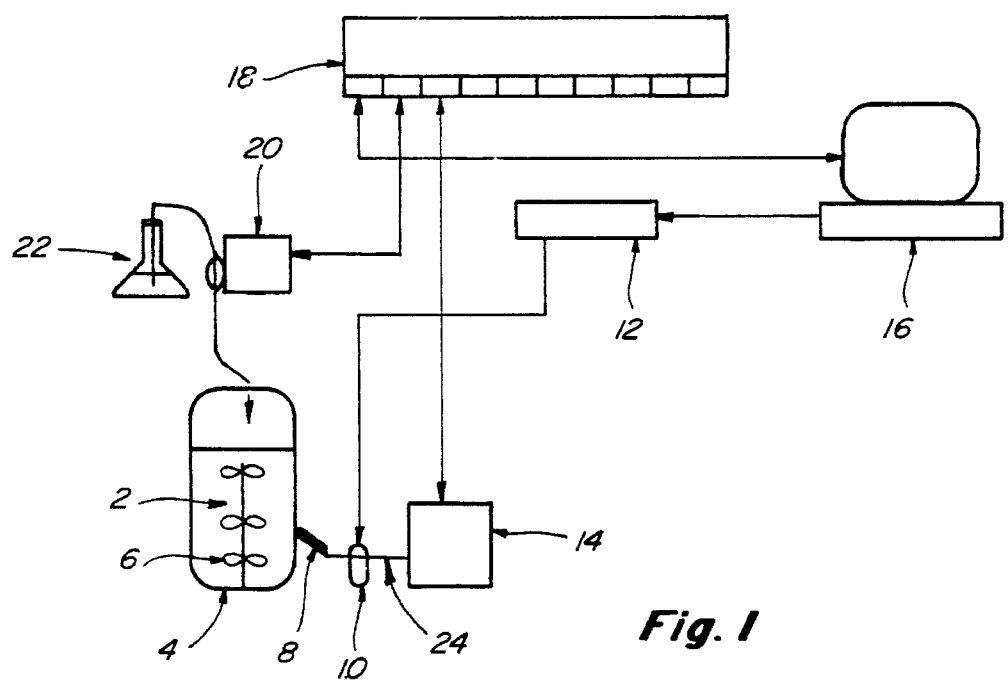
FIG. 1 is a schematic representation of a single control system for glucose control.

The method of the present invention is shown schematically in FIG. 1. In short, samples of a fermentation broth (2) are periodically withdrawn from a fermentor (4) in which agitation means (6) maintains a generally consistent concentration throughout the broth, by a sampling device (8) by the periodically opening of a pinch or solenoid valve (10) via a solenoid swithching box (12) and are submitted to a nutrient concentration analyzer (14) to determine the nutrient concentration of the sample. The concentration data are fed to a computer(16) preferably an "IBM XT, AT®" or compatible with "DOS version 2.0"® or higher, with at least one RS 232 port and a minimum of 350K RAM memory, via a multiplexor (18) preferably being an "Omega"® multiplexor which compares the concentration to that measured of an earlier sample, preferably the immediately preceding sample, to calculate the rate at which the nutrient was consumed over the period of time from the earlier sample to the most recent sample. This consumption rate is compared to earlier consumption rates determined in the same way. From this comparison, a consumption rate over the next time period (extending from the most recent sampling to the next sampling) is predicted by the computer (16) and a signal is sent from the computer (16) to a pump (20) preferably a "Masterflex"® computerized drive pump capable of communicating to the computer via the multiplexor (18) and to deliver the determined volume of nutrient stock (22) to the fermentation broth (2) to compensate for the predicted nutrient consumption and maintain the nutrient concentration at the desired level. The sampling frequency may also be controlled by the computer (16), which may further be programmed to catch errors by directing solenoid valve (10) to resample the fermentation broth (2) if the nutrient concentration of the sample differs too significantly from that expected or that of an earlier sample. The error ranges may be arbitrarily set depending upon the microorganism and the nutrient setpoint to be used during the fermentation.

Generally, the fermentation broth (whole broth) comprises microorganisms and a nutrient medium. The microorganisms typically are bacteria or yeast. Preferably the bacteria are *Escherichia coli, Bacillus subtilis* or *Serratia marcescens*. The yeast is preferably *Saccharomyces cerevisiae*.

The fermentation broth is agitated by means (6) to maintain access to the nutrient by the microorganisms. Sufficient agitation is also particularly important in the present invention to maintain generally uniform concentrations through the broth so that samples withdrawn therefrom fairly represent the entire broth.

It has been found that a superior technique for withdrawing broth (2) from the fermentor (4) is through a sampling valve (8), preferably being a "VANASYL SAMPLING VALVE"®, Vanasyl Valves, Ltd., Sheffield England. This sampling valve is an in-place sterilizable, aseptic spindle valve which is attached, through a small orifice to thin silicone tubing (24) preferably being "Masterflex"® to withdraw a small sample (about 1–3 ml) of the broth for analysis. The sample may be withdrawn by opening a solenoid valve (10) set on the thin tubing (24) of the sampling device. Because back-pressure is maintained on the fermentation broth in the sparged fermentor (4), when the solenoid valve (10) is opened, broth (2) is forced through the orifice, into the tubing (24) and to a nutrient concentration analyzer (14) to which the sampling device is also attached. Alternatively or additionally, the nutrient concentration analyzer (14) can apply a vacuum to pull broth to the analyzer.

Upon opening of the valve (10) of the sampling device, flow from the thin tubing (24) is first directed away from or outwardly from the analyzer (14), thus flushing the tubing of the stagnant broth remaining in the tubing to a waste container located in the analyzer (14). Then, flow is redirected to introduce a sample of fresh broth (2) to the analyzer after which the solenoid valve (10) is closed. The intervals between samples may be selected as desired, with shorted intervals generally being associated with greater precision in maintaining the nutrient concentration level. All of these functions may be controlled by computer.

This on and off sampling technique has been found to permit the withdrawal and sampling of such minor volumes of broth (1–3 ml samples have been found to be possible and sufficient), that frequent sampling can be achieved without depleting the broth. For example, samples may be taken two minutes or five minutes apart, as desired, without the volume withdrawn exceeding the volume of nutrient being added.

When the nutrient is glucose, it has been found that a "YSI Model 2000 Glucose and L-Lactate Analyzers"® is particularly well suited for use as the nutrient concentration analyzer (14) for a number of reasons: 1) "The YSI Model 2000 analyzer"® is a microprocessor based analyzer which is computer compatible with an RS-232 interface; 2) it is capable of sample aspiration and it can accurately measure glucose concentrations in a small volume (0.5 mls) of whole broth without the need for separating cells from the broth; 3) glucose measurements can be made over a wide range of glucose concentrations (0 to 20 grams per liter); 4) it is self-calibrating which improves the precision of measurements to within +/–2.0% or 0.04 grams per liter; 5) the sample response time required for the measurement is 60 seconds, an advantage for fast control response; 6) it is capable of using two glucose oxidase membranes to enzymatically determine glucose concentration, but one membrane is sufficient for control purposes.

Figure 3A:
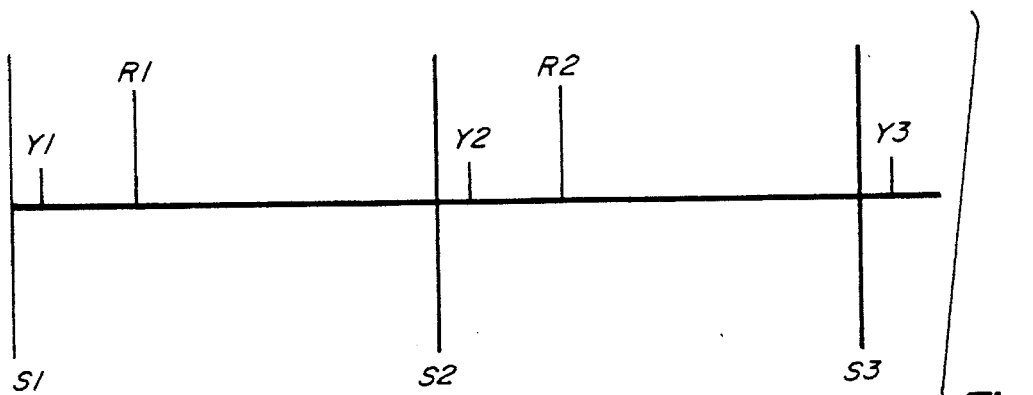
Figure 4A:
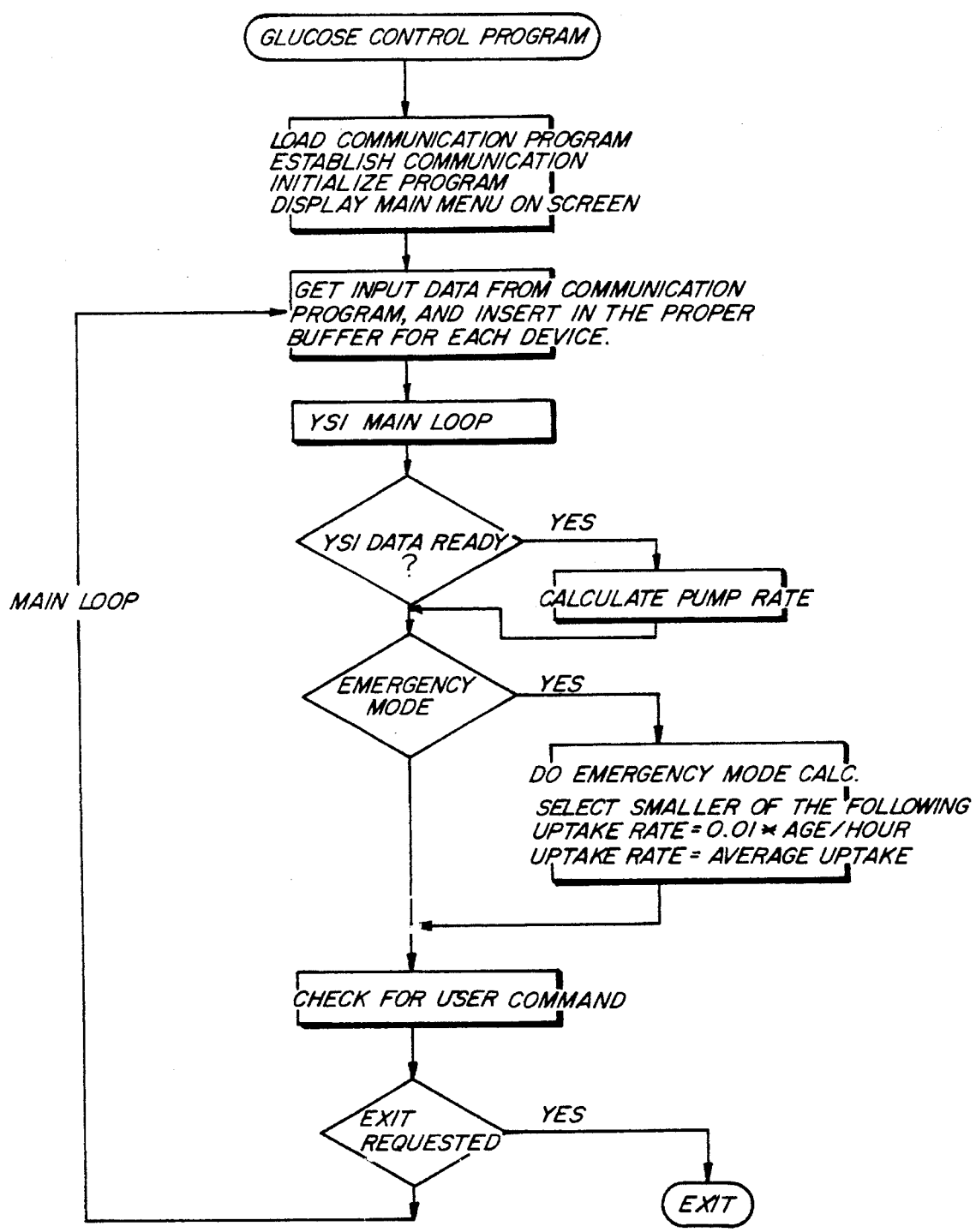
FIG. 4a, 4b, 4c is a program flow chart for the method of the present invention.
Figure 4B:
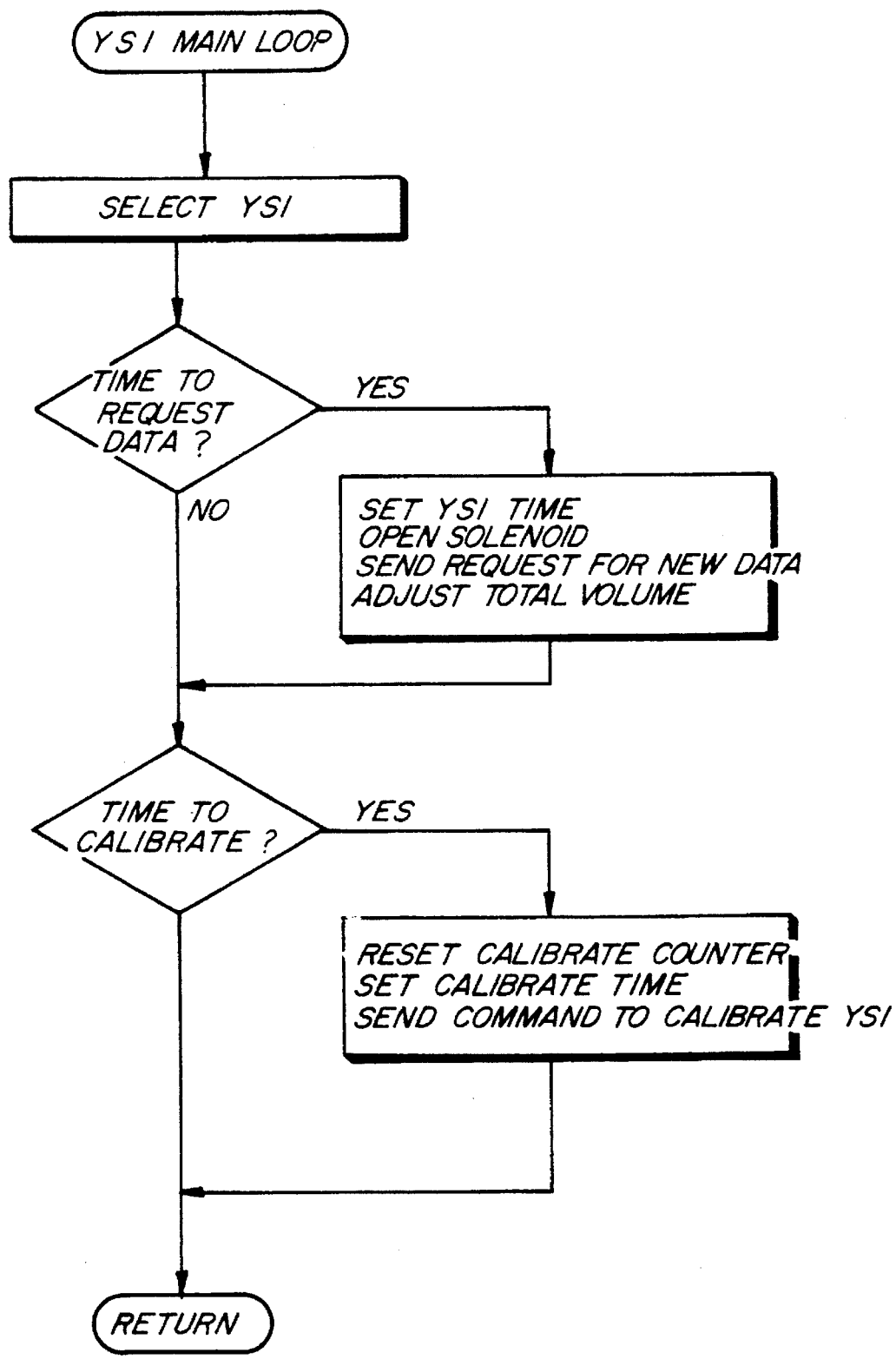
Figure 4C:
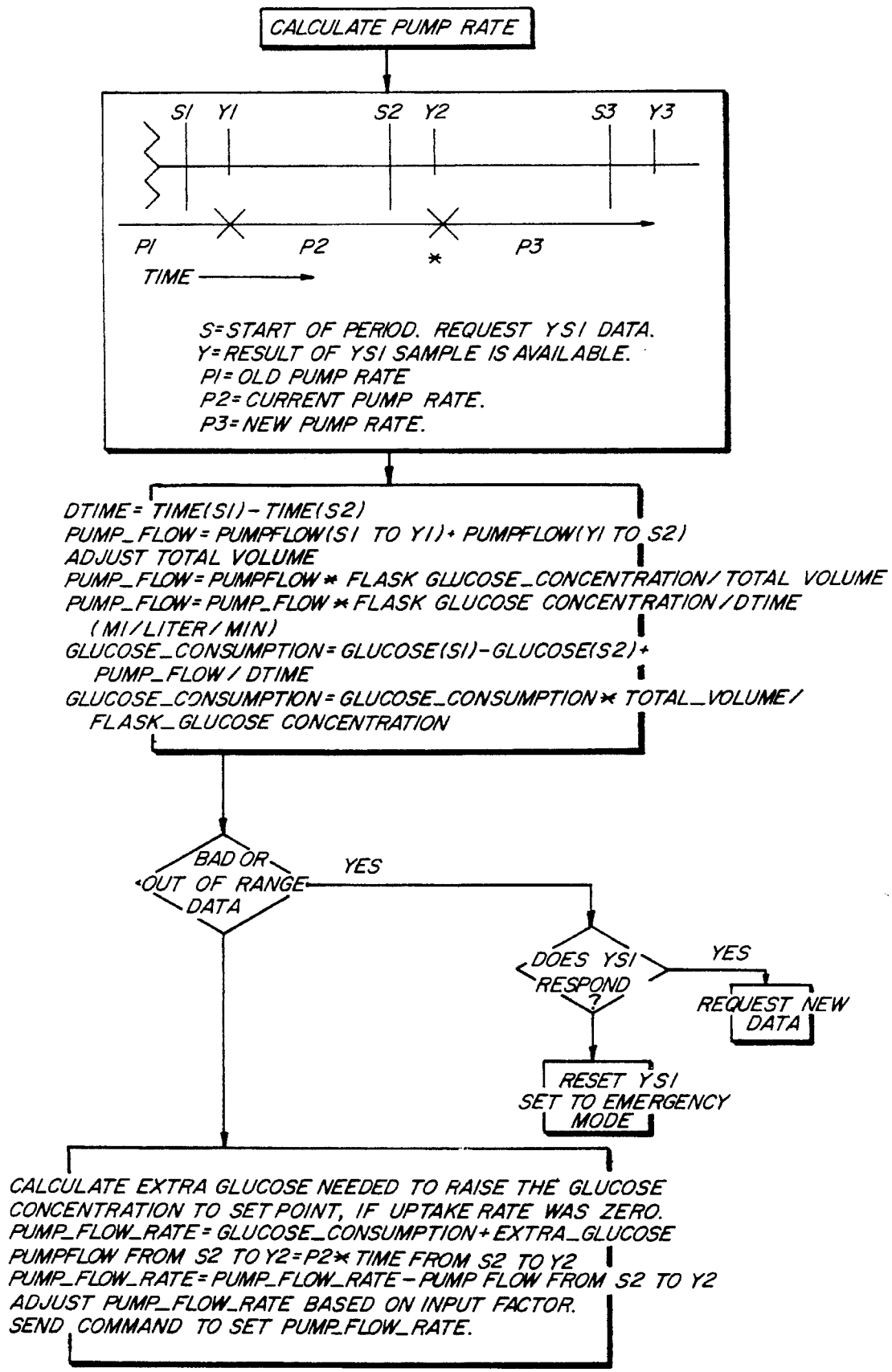

There are several methods for calculating the glucose consumption rate which known in the art but the preferred method and formulas are shown in FIG. 3a and 3b. The computer performs these functions as shown in FIG. 4a, 4b, and 4c.: 1) it compares the glucose concentration of the sample (Y2) to that of an earlier sample, preferably the next previous sample (Y1), 2) it calculates the amount of glucose added over the time interval and 3) calculates the rate at which the nutrient was consumed over that time interval.

A further error-check method requires the computer to compare that rate to rates determined in like fashion for preceding intervals, preferably the rate is compared to the average of the four immediately preceding intervals to develop a profile of the change in consumption rate over time.

From this comparison, the consumption rate over that next interval is predicted and glucose setpoint control is achieved with the formulas shown in FIGS. 3a and 3b. First, setpoint correction is calculated by comparing the measured concentration (Y2) to the predetermined setpoint. Second, the amount of glucose required to adjust the glucose concentration (Y2) to the predetermined setpoint is calculated and the desired amount of glucose is delivered via the new pump rate. Further, an error compensation factor, calculated by using a gain constant (K), modifies the newly corrected flow rate either positively or negatively, depending upon whether the measured glucose concentration is higher or lower than the setpoint.

The computer may further be programmed to recognize sampling or measurement errors. If the measured nutrient concentration falls outside a preselected range from the predicted nutrient concentration or the nutrient concentration measured for the previous sample, the computer discounts that sample and directs a new sample to be withdrawn. The error ranges will probably differ depending on the organism being grown in the fermentor and by the vessel size since the mixing characteristics of the fermentors vary with size. The computer (16) may also be programmed to maintain high analyzer precision by instructing the analyzer to recalibrates periodically, such as after every fifth sample or every fifteen minutes. The program may further enable the computer to recognize inappropriate shutdowns of the analyzer, at which point it would instruct the analyzer to restart.

Figure 2:
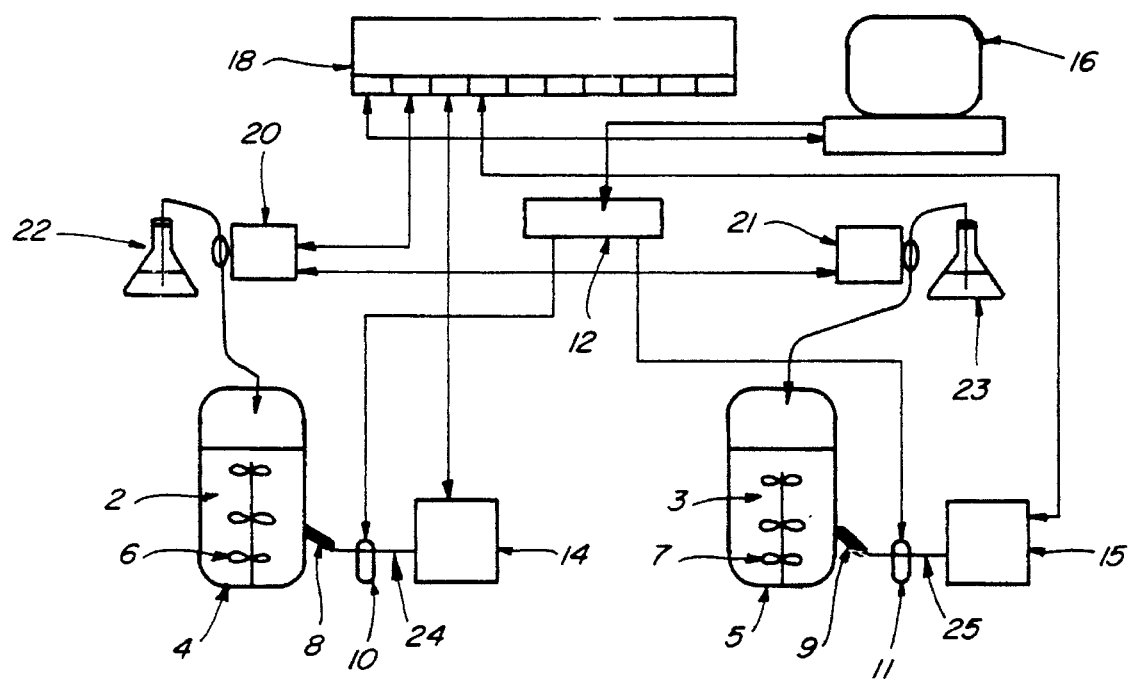
FIG. 2 is a schematic representation of a multiple control broth glucose control.

The method of the present invention also includes the ability to control more than one fermentation process simultaneously, shown schematically in FIG. 2. When two or more fermentation processes are controlled by the invention, one additional hardware modification is made. The nutrient pumps (20, 21) which contain RS232 ports are serially connected, allowing the computer (16) to communicate with nutrient pump (21) and nutrient pump (20) via the multiplexor (18). Upon completion of a control action from the current process, additional processes are accommodated and prioritized on a timed, sequential basis. While additional processes are waiting for updated control actions by the computer (16), nutrient feed rates continue at the previously calculated The control process of this invention has been found to allow greater control sensitivity than has been achieved with conventional manual control techniques, and this superior sensitivity has been accomplished with much faster response to deviations of nutrient concentration from desired levels. Moreover, because of the automated nature of the process of the present invention, substantial labor savings are provided over the manual methods.

Highly sensitive control is afforded without the need for comparative tests or an archive of nutrient consumption rate profiles. Accordingly, as compared to other techniques known in the art, the method of the present invention provides a highly flexible control system applicable to fermentations even of untested strains of microorganisms, regardless of the fermentation conditions or disturbances or changes in conditions. When the broth is disturbed, causing a discontinuity in the consumption rate profile, a sudden change in nutrient concentration or some other nonstandard consumption rate profile, the control technique of this invention quickly adapts and reins in or controls the nutrient concentration to yield desired level.

The method of the present invention is far more flexible than that known in the art and is applicable even to unusual bacterial strains (including recombinant strains) or other microorganisms under unusual or varying conditions, and is particularly suitable for production of proteins—a prime reason for carrying out fermentation. In protein production, two fermentations are effectively carried out. The first fermentation increases bacterial density. Then, when protein production is induced, a discontinuity in nutrient consumption results, followed by commencement of what is effectively a second fermentation. The present invention can adapt to this nonstandard consumption rate profile—it is not limited to the comparison to standard profiles.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

Figure 5:
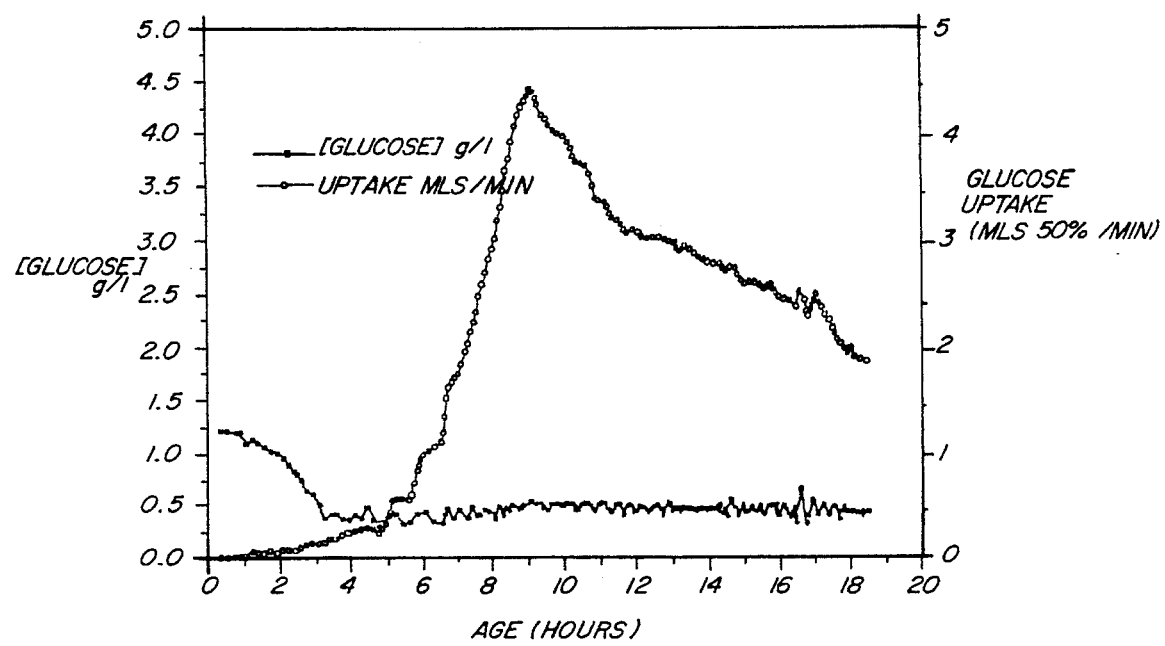
FIG. 5 is a typical glucose control profile.

A typical glucose control profile resulting from the invention is shown in FIG. 5. The example shown was a profile generated from an *E. coli* fermentation producing the rDNA protein Porcine Somatotropin (PST). Glucose was initially batched in the fermentation at 3.4 g/l and allowed to be depleted until it reached the glucose control setpoint of 0.5 g/l. Glucose concentration was maintained at 0.5 g/l+/−0.20 g/l throughout the fermentation. Glucose uptake rate (mls of 50% glucose feed solution/min) is also plotted in this profile. It can be seen that even when glucose utilization changed dramatically during induction (age=10 hrs.) glucose control was unaffected. Final Dry Cell Weight was 31.5 g/l.

EXAMPLE 2

*E. coli* strains containing plasmids for the production of three rDNA proteins were run under identical fermentation conditions except for glucose setpoint control as shown in Table 1. The rDNA proteins were porcine somatotropin (PST), bovine placental lactogen (BPL) and bovine prolactin (BPRL). Glucose setpoints were controlled at 0.2 grams/liter (g/l), 1.0 g/l, 2.5 g/l, 5.0 g/l and 10.0 g/l. Samplings were made at 5 minute intervals, and the pans were carried out for 18 hours. The concentration of glucose in the feed stream was 0.50 g/l and the starting concentration of bacteria in each culture was 0.3–0.5 g/l. At the end of the runs, the glucose conversion efficiency, i.e., grams of biomass produced per gram of glucose consumed (g. DCW/g. Glucose) were measured by reference. The experimental results (Table 1) show that glucose conversion efficiency is 1) highest when glucose concentration is controlled at very low concentrations, and 2) is independent of the heterologous protein being produced.

TABLE 1

| Glucose Setpoint(g/l) | Glucose Conversion Efficiency (g. DCW/g.Glucose) | | |
|---|---|---|---|
| | PST | BPL | BPRL |
| 0.2 | 0.321 | 0.43 | 0.65 |
| 1.0 | 0.277 | 0.32 | 0.55 |
| 2.5 | 0.252 | 0.31 | 0.52 |
| 5.0 | 0.250 | 0.29 | 0.50 |
| 10.0 | 0.247 | 0.26 | 0.48 |

EXAMPLE 3

In the case of the BPL and BPRL fermentations it was discovered that the glucose setpoint was a critical parameter in optimizing production of these rDNA proteins. The yield of BPL is expressed as the percentage of total cellular protein made as BPL (%TCP) and was determined by spectrophotometric scanning of an SDS-PAGE gel. The yield of BPRL is expressed in grams per liter (g/l) and was determined by high performance liquid chromatography (HPLC). Results are shown in Table 2.

TABLE 2

| Glucose Setpoint (g/l) | % TCP BPL | g/l BPRL |
|---|---|---|
| 0.0 (starvation) | 4.5 | 1.14 |
| 0.2 | 20.0 | 1.46 |
| 1.0 | 9.0 | 1.54 |
| 2.5 | 8.0 | 1.27 |
| 5.0 | 8.0 | 1.10 |
| 10.0 | 7.0 | 0.65 |

EXAMPLE 4

To further demonstrate generic capability of the method to perform equally well with other industrially important microorganisms, fermentations were run with the bacteria *Bacillus subtilis and Serratia marcescens*, and the yeast *Saccharomyces cerevisiae*. The *Bacillus subtilis* fermentation media or nutrient was Luria Broth, a complex medium which generated high glucose conversion efficiencies because of its high nitrogen source content. The *Serratia marcescens* fermentation media consisted of M9 and 2% casamino acids, and the *Saccharomyces cerevisiae* fermentation media consisted of yeast extract-peptone-dextrose (YEPD). All three microorganisms were grown in fermentations where the glucose setpoints were 0.5 g/l, 5.0 g/l and 10.0 g/l. These results shown in Table 3 demonstrate that the invention can be used to optimize glucose conversion efficiency for a variety of microorganisms.

TABLE 3

| Glucose Setpoint(g/l) | Glucose Conversion Efficiency (g. DCW/g.Glucose) | | |
|---|---|---|---|
| | Bacillus s. | Serratia m. | Saccharomyces c. |
| 0.5 | 1.250 | 0.220 | 0.074 |
| 5.0 | 0.898 | 0.217 | 0.060 |
| 10.0 | 0.437 | 0.271 | 0.069 |

In view of the above, it will be seen that the several advantages of the invention are achieved and other advantageous results attained. As various changes could be made in the above methods and compositions without departing from the scope of the invention, it is intended that all matter contained in the above description and shown in the accompanying drawing shall be interpreted as illustrative and not in a limiting sense.

What is claimed:

1. A method for controlling nutrient concentration levels in a broth, comprising the steps of:
   a. fermenting a broth containing a bacteria or a yeast and a nutrient;
   b. withdrawing a series of samples of said broth at periodic intervals, said series of samples comprising a first sample, a second sample, a third sample, and a fourth sample;
   c. measuring the nutrient concentrations of said samples;
   d. transferring said nutrient concentration measurements to a computer which can calculate the nutrient consumption rate of said broth for the interval of time between said first sample and said second sample, and between said second sample and said third sample, in real time, by comparing the nutrient concentration of a sample to the nutrient concentration of a preceding sample;
   e. using said computer to predict an estimated rate at which the nutrient concentration of said broth is expected to decrease during an interval of time between said third sample and said fourth sample by comparing said nutrient consumption rate at which the nutrient concentration of said broth decreased between said second sample and said third sample to the rate at which the nutrient concentration of said broth decreased between said first sample and said second sample; and
   f. adding fresh nutrient to the broth at a rate and quantity based on said estimated rate.

2. The method of claim 1 wherein the bacteria are *Escherichia coli, Bacillus subtilus, or Serratia marcescens*.

3. The method of claim 1 wherein the yeast is *Saccharomyces cerevisiae*.

4. The method of claim 1, further comprising the step of determining whether the nutrient concentration measured in a sample deviates from an expected value by more than a preselected amount, and if the concentration does so deviate, comprising the futher step of withdrawing a new sample of the broth and measuring the nutrient concentration of the new sample and determining the calculated rate by comparing of the nutrient concentration of the new sample with that of the preceding sample.

5. The method of claim 1, wherein said broth is whole broth.

6. The method of claim 2, wherein said *E. coli* is grown at a nutrient setpoint of 0.20 grams per liter for optimum glucose conversion efficiency.

7. The method of claim 6, wherein said nutrient is glucose.

8. The method of claim 3, wherein said *E. coli* is grown at a nutrient setpoint of 0.20 grams per liter for optimum production of rDNA proteins.

9. The method of claim 1 further comprising fermenting a plurality of broths and said plurality of broths being controlled by said computer.

Figure 3A:
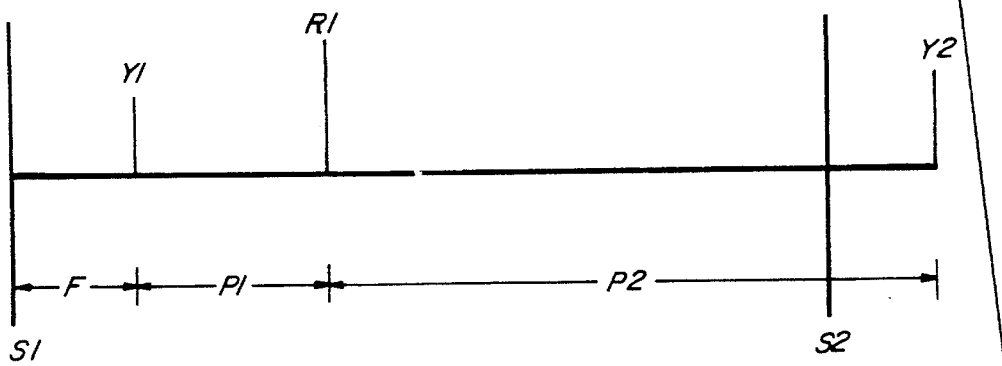

10. The method of claim 1 wherein said estimated rate is achieved using the glucose setpoint control equations shown in FIG. 3$b$.

11. The method of claim 8, wherein said rDNA proteins are bovine prolactin or bovine placental lactogen.

12. A fermentation nutrient control system comprising:
   a. means for withdrawing a series of samples of a fermentation broth at periodic intervals, said series of samples comprising a first sample, a second sample, and a third sample;
   b. means for measuring nutrient concentrations of said samples;
   c. computer control means for calculating in real time a nutrient consumption rate of said broth for the interval of time between said first sample and said second sample and between said second sample and said third sample, by comparing the nutrient concentration of a sample to the nutrient concentration of a preceding sample;
   d. computer control means for predicting the nutrient consumption rate of said broth for the interval of time between said third sample and a fourth sample by comparing said nutrient consumption rate at which the nutrient concentration of said broth decreased between said second sample and said third sample to the rate at which the nutrient concentration of said broth decreased between said first sample and said second sample; and
   e. means for adding fresh nutrient to the broth at a rate and quantity based on said predicted nutrient consumption rate.

* * * * *